US00PP29093P3

(12) United States Plant Patent
Sidhu

(10) Patent No.: US PP29,093 P3
(45) Date of Patent: Mar. 13, 2018

(54) ***GAULTHERIA* PLANT NAMED 'GAULSIDH5'**

(50) Latin Name: *Gaultheria procumbens*
Varietal Denomination: Gaulsidh5

(71) Applicant: Gurjit Sidhu, Mission (CA)

(72) Inventor: Gurjit Sidhu, Mission (CA)

( * ) Notice: Subject to any disclaimer, the term of this patent is extended or adjusted under 35 U.S.C. 154(b) by 0 days.

(21) Appl. No.: 15/330,619

(22) Filed: Oct. 19, 2016

(65) Prior Publication Data

US 2017/0142883 P1 May 18, 2017

(30) Foreign Application Priority Data

Nov. 17, 2015 (CA) ..... PBR 15-8750

(51) Int. Cl.
*A01H 5/08* (2006.01)

(52) U.S. Cl.
USPC ..... Plt./226

(58) Field of Classification Search
USPC ..... Plt./226
CPC ..... A01H 5/02; A01H 5/00; A01H 5/08
See application file for complete search history.

*Primary Examiner* — June Hwu
(74) *Attorney, Agent, or Firm* — Penny J. Aguirre

(57) ABSTRACT

A new cultivar of *Gaultheria procumbens* plant named 'Gaulsidh5' that is characterized by its berries that are red-pink in color and very large in size and its moderately vigorous growth habit.

2 Drawing Sheets

Botanical classification: *Gaultheria procumbens.*
Cultivar designation: 'Gaulsidh5'.

CROSS REFERENCE TO RELATED APPLICATIONS

This application is co-pending with U.S. Plant Patent Applications filed for plants derived from the same breeding program that are entitled *Gaultheria* Plant Named 'Gaulsidh11' (U.S. Plant patent application Ser. No. 15/330,620).

BACKGROUND OF THE INVENTION

The present invention relates to a new and distinct cultivar of *Gaultheria procumbens*, known as *Gaultheria* 'Gaulsidh5' and is hereinafter referred to by its cultivar name 'Gaulsidh5'.

'Gaulsidh5' originated from the open pollination of unnamed and unpatented seedlings of *Gaultheria procumbens* in the Inventor's greenhouse production bed in Mission, B.C., Canada. The exact parentage is therefore unknown. 'Gaulsidh5' was selected as a single unique plant in 2011 from amongst the resulting seedlings.

Asexual reproduction of the new cultivar was first accomplished by tissue culture using meristemac tissue under the direction of the Inventor in Mission, B.C., Canada in April of 2011. Asexual propagation of the new cultivar by tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Gaulsidh5' as a new and unique cultivar of *Gaultheria.*

1. 'Gaulsidh5' exhibits berries that are red-pink in color and very large in size.
2. 'Gaulsidh5' exhibits a moderately vigorous growth habit.

Typical plants of the parent species of 'Gaulsidh5', *Gaultheria procumbens*, are similar to 'Gaulsidh5' in having similar foliage. Typical plants of *Gaultheria procumbens* differ from 'Gaulsidh5' in having berries that are smaller in size and a more vigorous growth habit. 'Gaulsidh5' can be most closely compared to *Gaultheria procumbens* 'Gaulsidh11'. 'Gaulsidh11' differs from 'Gaulsidh5' in having a more vigorous growth habit, improved berry set and leaves that are longer in length.

BRIEF DESCRIPTION OF THE DRAWINGS

The accompanying colored photographs illustrate the overall appearance and distinct characteristics of the new *Gaultheria*. The photographs were taken of a plant about 6-months in age as grown outdoors in a 4-inch containers in Elma, Wash.

The photograph in FIG. 1 provides a top view and a side view of the plant habit of 'Gaulsidh5'.

Figure 1:
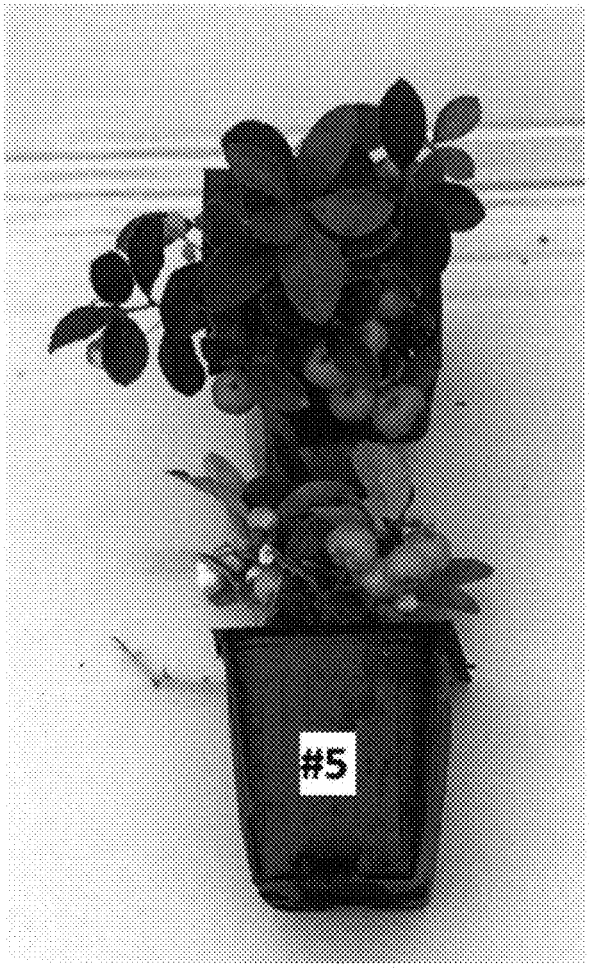
Figure 2:
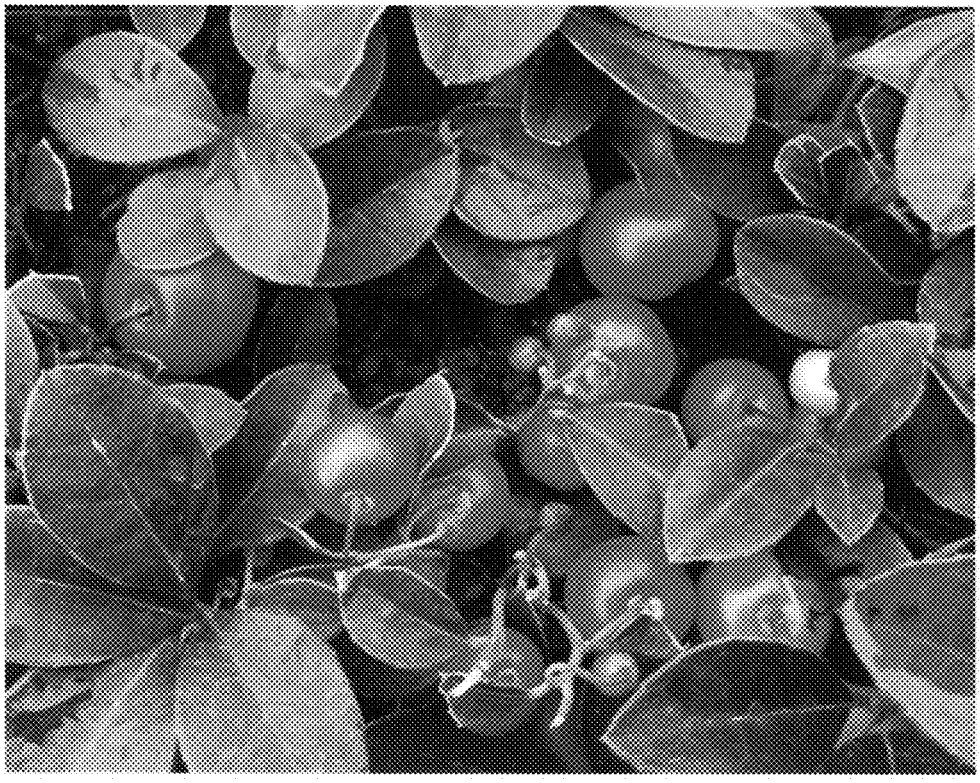

The photograph in FIG. 2 provides a close-up view of the fruit of 'Gaulsidh5'.

The colors in the photographs may differ slightly from the color values cited in the detailed botanical description, which accurately describe the colors of the new *Gaultheria.*

DETAILED BOTANICAL DESCRIPTION OF THE PLANT

The following is a detailed description of six month-old plants of the new cultivar grown outdoors in 4-inch containers in Elma, Wash. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—Late spring to late summer in B.C., Canada.

*Plant type.*—Evergreen shrub.

*Plant habit.*—Broadly spreading, groundcover once established.

*Height and spread.*—9 cm in height and 15 cm in width as a grown in a 4-inch container.

*Cold hardiness.*—At least in U.S.D.A. Zones 3 to 8.

*Diseases and pests.*—No resistance or susceptibility to diseases or pests has been observed.

*Propagation.*—Tissue culture.

*Root development.*—An average of 6-months to to fully root in a 4-inch container from a plug produced by tissue culture.

*Growth rate and vigor.*—Moderate.

Stem description:

*Shape.*—Round.

*Stem color.*—New and mature growth; a blend of 144A and 184A.

*Stem size.*—An average of 5 cm in length and 1 mm in width.

*Stem surface.*—Young stems moderately glossy.

*Branching.*—Freely branched, an average of 10 basal branches.

*Branch angle.*—Upright to outward.

*Branch internode length.*—Up to 1 cm.

Foliage description:

*Leaf shape.*—Obtuse.

*Leaf division.*—Simple.

*Leaf base.*—Acute.

*Leaf apex.*—Broadly acute.

*Leaf fragrance.*—Wintergreen if crushed.

*Leaf venation.*—Pinnate, not conspicuous, upper and lower surface match leaf surface, middle vein on upper surface turns 182A from mid section to base.

*Leaf margins.*—Very slightly and irregularly serrate, one small hair emerging from the tip of teeth, up to 1 mm in length and 182A in color.

*Leaf arrangement.*—Alternate and clustered near tips.

*Leaf attachment.*—Petiolate.

*Leaf number.*—Average of 9 per branch.

*Leaf surface.*—Upper and lower surface; glabrous, glossy and leathery.

*Leaf size.*—Average of 4.5 cm in length 3 cm in width.

*Leaf color.*—Young and mature leaves upper surface; a blend of 136A and 137A, young and mature leaves lower surface; a blend of 138B, 148C and an overlay of 182B to 182C with overlay more pronounced in winter.

*Petioles.*—Average of 6 mm in length and 2 mm in width, upper and lower surfaces are dull, color; upper and lower surfaces 183A with areas of 182A.

*Stipules.*—None observed.

Inflorescence description:

*Inflorescence.*—Axillary and terminal clusters of individual flowers.

*Inflorescence size.*—Average of 2 cm in length and 3 cm in width.

*Lastingness of inflorescence.*—Average of 2 weeks, self cleaning (sepals and petals).

*Number of flowers.*—1 to 4 per panicle, average of 30 per plant.

*Flower buds.*—Ovate in shape, average of 8 mm in length and 4 mm in width, a blend of 156C and NN155D in color, satiny surface.

*Flower size.*—Average of 1 cm in length and 6 mm in width.

*Corolla.*—Urceolate in shape, comprised of 5 fused ovate shaped petals with rounded tips (5%) free that are curled under, free curled parts are 1 mm in length and width, color a blend of 156C and NN155D on both surfaces when opening and mature, both surfaces are satiny and glabrous, very slightly ribbed on inner and outer surfaces.

*Calyx.*—Rotate in arrangement, average of 3 mm in depth and 6 mm in diameter.

*Sepals.*—5, ovate in shape with base fused (lower 25% fused into ring), average of about 3 mm in length and 2 mm in width, acute apex, NN155A in color, satiny on both surfaces.

*Bracts.*—2 small bracts, an average of 1 mm in length and width, ovate in shape, truncate base, acute apex, glossy on both surfaces, 144A in color.

*Peduncles.*—Round, curved to hang downward, an average of 1.2 cm in length and 1 mm in width, 138B and suffused with 178B in color, pubescent surface.

*Pedicels.*—None, peduncles arise directly from stem node.

Reproductive organs:

*Androecium.*—Average of 10 stamens, anthers are dorsifixed, narrow deltoid in shape, N199C in color and 2 mm in length, filaments oblong in shape are 4 mm in length, 1 mm in width and NN155C in color and suffused with 73C towards base, highly pubescent, pollen is moderate in quantity and NN155C in color.

*Gynoecium.*—1 pistil, stigma is club-shaped, 1 mm in length and width, and 145D in color, style is an average of 6 mm in length and 157D in color, ovary is round in shape, 6-parted, 2.5 mm in diameter and depth, and 145C in color.

Fruit description:

*Type.*—Berry.

*Number.*—Average of 3 per lateral branch.

*Fruit size.*—Up to 1.5 cm in length and 2 cm in width.

*Fruit skin color.*—Young fruit; a blend of 69D and 62A, mature fruit; 42A.

*Fruit flesh.*—NN155D in color, glistening and spongy in texture.

*Fruit surface.*—Glossy and glabrous.

*Fruit shape.*—Rounded with indented apex and 5 bluntly acute extended tips, tip size is 5 mm in length and 8 mm in width.

*Seeds.*—Few cylindrical shaped seeds, glossy surface, less than 1 mm in length and width, 150D in color.

It is claimed:

1. A new and distinct cultivar of *Gaultheria* plant named 'Gaulsidh5' as herein illustrated and described.

* * * * *